United States Patent [19]
Gagnebien

[11] Patent Number: 5,858,380
[45] Date of Patent: Jan. 12, 1999

[54] STABLE GELLED COMPOSITION WITH A HIGH ELECTROLYTE CONTENT

[75] Inventor: Didier Gagnebien, Westfield, N.J.

[73] Assignee: L'Oreal, Paris, France

[21] Appl. No.: 815,514

[22] Filed: Mar. 12, 1997

[30] Foreign Application Priority Data

Mar. 12, 1996 [FR] France .................................. 96-03094

[51] Int. Cl.$^6$ ...................................................... A61K 7/40
[52] U.S. Cl. ........................ 424/401; 424/400; 424/485; 424/488; 424/70.13; 514/937; 514/779; 514/780; 514/781; 514/782
[58] Field of Search ................................ 424/70.13, 400, 424/401, 485, 488, 70.1, 61, 59, 47, 63, 65, 69, 70.8, 70.9, 73, 78.02, 78.03, 78.05, 78.06, 78.07; 514/937–944, 779–782; 536/52

[56] References Cited

U.S. PATENT DOCUMENTS

| | | | |
|---|---|---|---|
| 4,401,760 | 8/1983 | Peik et al. | 435/101 |
| 4,870,167 | 9/1989 | Zody et al. | 536/114 |
| 5,653,970 | 8/1997 | Vermeer | 424/70.24 |
| 5,723,112 | 3/1998 | Bowser et al. | 424/70.13 |

*Primary Examiner*—Neil S. Levy
*Attorney, Agent, or Firm*—Oblon, Spivak, McClelland, Maier & Neustadt, P.C.

[57] ABSTRACT

A stable gelled composition is provided which can contain a large amount of electrolyte and which contains, as gelling agent, a polysaccharide alkyl ether formed from units containing at least two different monosaccharides, each unit containing at least one saturated alkyl ether group. The polysaccharide alkyl ether preferably has a molecular weight of greater than 200,000 and is in particular a guar gum alkyl ether having a degree of substitution of approximately 2 to 3, preferably about 2.5. The composition obtained can be used in the cosmetics and/or dermatological fields for the treatment and care of the skin, scalp, mucous membranes, nails and hair.

16 Claims, No Drawings

5,858,380

STABLE GELLED COMPOSITION WITH A HIGH ELECTROLYTE CONTENT

BACKGROUND OF THE INVENTION

FIELD OF THE INVENTION

The present invention relates to a stable gelled composition, in particular a topical composition, which can contain a large amount of electrolyte, and to its use, in particular for the treatment and care of the skin, scalp, mucous membranes, nails and hair.

DISCUSSION OF THE BACKGROUND

It is known in the cosmetics, dermatological and pharmaceutical fields to use topical compositions in the form of gels or emulsions containing gelling agents which give consistency to these compositions. The majority of the gelling agents conventionally used are aqueous gelling agents and in particular carboxyvinyl polymers, which are neutralized with a base.

However, certain compounds which are desirable to use in these compositions do not, as a result of incompatibility, allow the above-mentioned gelling agents to be employed.

It is known, for example, that electrolytes (inorganic and organic salts) "break down" emulsions gelled with carboxyvinyl polymers and liquify them. Compositions containing carboxyvinyl polymers and electrolytes thus lack consistency, which conflicts with the result sought after by the use of a gelling agent.

Now, it may be desirable to introduce electrolytes into thickened compositions, in particular topical compositions, and sometimes even in a relatively large amount, in particular when these electrolytes have a beneficial effect on the skin or hair.

One solution consists in using, instead of carboxyvinyl polymers, gelling agents of a polysaccharide type, such as guar or xanthan gums or cellulose derivatives. EP-A-654, 270 thus describes a topical composition intended for the treatment of acne and seborrhoeic dermatitis containing a mixture of salts and, as gelling agent, a cellulose derivative, such as hydroxyethyl cellulose.

Unfortunately, the compositions based on cellulose derivatives in accordance with this document, and in particular the aqueous gels not containing a fatty or oily phase, do not have a smooth texture and, on the contrary, have a granular appearance which is not very pleasing to the eye. In addition, they leave the skin "as wet" after application, because these compositions do not penetrate sufficiently into the skin. All this proscribes their use in the cosmetics and/or dermatological fields.

The combination of these cellulose derivatives with another thickening agent, such as a silicate, as described, for example, in WO-A-93/8230, gives compositions which possess the same disadvantages as indicated above (granular appearance).

There thus remains the need for gelled compositions containing electrolytes which do not exhibit the disadvantages encountered with known gelling agents, in particular thin consistency, instability, granular appearance, unpleasant feel to the touch and incompatibility with these electrolytes.

SUMMARY OF THE INVENTION

One object of the present invention is consequently a composition containing at least one electrolyte and an oily phase containing at least one gelling agent, the gelling agent being a polysaccharide alkyl ether formed from units containing at least two different monosaccharide rings, each unit containing at least one hydroxyl group substituted by a saturated hydrocarbon alkyl chain (a saturated alkyl ether group).

DETAILED DESCRIPTION OF THE PREFERRED EMBODIMENTS

The gelling agent according to the invention is a gelling agent for oils, that is to say capable of thickening oily phases. The composition according to the invention can just as easily be an oily gel as a water-in-oil or oil-in-water emulsion or a dispersion of oil in water with lipid vesicles.

According to a specific embodiment of the invention, the polysaccharide alkyl ether has a weight average molecular weight of greater than 100,000, and preferably of greater than 200,000. Each saccharide unit can contain from one to six and preferably from two to four hydroxyl groups substituted by a saturated alkyl chain.

The term "saturated alkyl chain" means a straight-chain or branched chain hydrocarbon containing from 1 to 24, preferably from 1 to 10 and better still from 1 to 5 carbon atoms. In particular, the alkyl chain is chosen from methyl, ethyl, n-propyl, isopropyl, n-butyl, isobutyl, tert-butyl and n-pentyl chains.

The monosaccharide rings are chosen in particular from mannose, galactose, glucose, furanose, rhamnose and arabinose.

According to a preferred embodiment of the invention, the polysaccharide alkyl ether according to the invention is an alkyl ether of a gum and more particularly of a gum which is overall non-ionic, that is to say substantially without ionic groups. Mention may be made, as appropriate gums, for example, of guar gum, the unit of which comprises a galactose and a mannose; locust bean gum, the unit of which comprises a galactose and a mannose; karaya gum, which is a complex mixture of rhamnose, galactose and galacturonic acid; or gum tragacanth, which is a complex mixture of arabinose, galactose and galacturonic acid.

According to a preferred embodiment of the invention, the polysaccharide alkyl ether is a derivative of guar gum and more particularly ethylated guar gum having a degree of substitution of approximately 2 to 3, preferably about 2.5, as described in Majewics et al, Research Disclosure No. RD 378007, page 642 (October 1995).

The composition according to the invention can contain, for example, an amount of polysaccharide alkyl ether ranging from 0.5 to 10 wt. %, and preferably from 2 to 8 wt. %, of the total weight of the composition.

The electrolyte can be present in the composition in particular in an amount ranging from 0.5 to 40% by weight, and preferably from 1 to 20% by weight, with respect to the total weight of the composition and may be present as an aqueous salt solution, for example.

Preferred electrolytes which can be used in the composition according to the invention include salts of mono-, di- or trivalent metals and more particularly alkaline-earth metal salts and in particular barium, calcium and strontium salts, alkali metal salts and, for example, sodium and potassium salts, as well as magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon and selenium salts, and their mixtures.

The anions of these salts can be chosen, for example, from carbonates, bicarbonates, sulfates, glycerophosphates, borates, chlorides, nitrates, acetates, hydroxides, persulfates and salts of α-hydroxy acids (citrates, tartrates, lactates or malates) or of fruit acids, or alternatively salts of amino acids (aspartate, arginate, glycocholate or fumarate).

The salt is preferably chosen from calcium, magnesium or strontium nitrate, calcium or magnesium borate, calcium, sodium, magnesium, strontium, neodymium or manganese chloride, magnesium or calcium sulfate, calcium or magnesium acetate, and their mixtures.

The composition according to the invention is applied in all fields where it is desired to obtain a thickened composition in the presence of electrolytes and in particular in the field of paints and in the farm-produce, cosmetics, dermatological and pharmaceutical fields.

The composition according to the invention is preferably intended for topical care or treatment. In this case, the composition must contain a topically acceptable medium, that is to say a medium which is compatible with the skin, the mucous membranes, the nails, the scalp and the hair. It can be provided in all pharmaceutical dosage forms appropriate for topical application and in particular in the form of a water-in-oil or oil-in-water emulsion or of an oily dispersion containing a small amount of water, loaded with electrolytes, dispersed in the oily phase. The composition according to the invention can also contain ionic and/or non-ionic lipid vesicles which may or may not contain a dispersed oil. It can constitute, for example, a cream or an ointment.

The amounts of the various constituents of the compositions according to the invention are those conventionally used in the field under consideration.

When the composition is an oily dispersion, the proportion of water dispersed in the oil is less than 10 wt. % and preferably less than 5 wt. %. The dispersed water can contain an amount of electrolytes ranging up to saturation.

When the composition of the invention is an emulsion, the proportion of the oily phase can range from 5 to 80% by weight, and preferably from 5 to 50% by weight, with respect to the total weight of the composition. The oils, the emulsifiers and the coemulsifiers used in the composition in the emulsion form are chosen from those conventionally used in the field under consideration. The emulsifier and the coemulsifier are present, in the composition, in a proportion ranging from 0.3 to 30% by weight, and preferably from 0.5 to 20% by weight, with respect to the total weight of the composition. The emulsion can additionally contain lipid vesicles.

In a known way, the composition of the invention can also contain adjuvants usual in the cosmetics and/or dermatological fields, such as active principles, preservatives, antioxidants, complexing agents, solvents, fragrances, fillers, screening agents, bactericides, odor absorbers and coloring materials. The amounts of these various adjuvants are those conventionally used in the field under consideration and, for example, from 0.01 to 20% of the total weight of the composition. These adjuvants, depending on their nature, can be introduced in the oily phase, in the aqueous phase and/or in the lipid vesicles.

Mention may be made, as oils which can be used in the invention, for example, of oils of vegetable origin, oils of animal origin, synthetic oils, and in particular fatty esters, and mixtures of these oils, as well as mixtures of these oils with silicone oils, fluorinated oils and/or mineral oils. Use may also be made, as fatty materials, of fatty alcohols (e.g., cetyl alcohol), fatty acids, waxes and waxy compounds.

Mention may be made, as emulsifiers which can be used in the invention, for example, of the mixture of glyceryl monostearate and of polyethylene glycol stearate sold by the company ICI under the name ARLACEL 165.

Mention may be made, as active principles which can be used in the invention, for example, of moisturizers, such as glycerol, or active principles for treating signs of ageing, acne, dermatitis or pigmentary blemishes.

The composition according to the invention can be used in particular for the treatment and the care of the skin, mucous membranes, nails, scalp and/or hair, in particular for the treatment of sensitive skin and of sensitive scalps and/or for moisturizing the skin.

Also within the scope of the present invention is a process for treating sensitive skin and/or sensitive scalps and/or for moisturizing the skin by applying an effective amount of the composition as defined above to the skin or scalp. For fuller details regarding sensitive skin, reference may be made to the document EP-A-680,749.

Further within the scope of the present invention is a process for the cosmetic and/or dermatological treatment of the skin, scalp, hair, nails and/or mucous membranes, characterized in that a composition as defined above is applied to the skin, scalp, hair, nails and/or mucous membranes.

EXAMPLE

The non-limiting example below of a composition according to the invention is constructively reduced to practice by way of illustration. The amounts are given therein as % by weight.

Example: Oil-in-water emulsion
Oily phase

| | |
|---|---|
| Pentaerythrityl tetraethylhexanoate (oil) | 0.45% |
| Cetyl alcohol | 0.075% |
| Coconut fatty acid diethanolamide (adjuvant) | 0.075% |
| ARLACEL 165, sold by the company ICI | 0.28% |
| Ethylated guar gum having a degree of substitution of approximately 2.5 | 3% |
| Aqueous phase: | |
| Strontium chloride | 2.8 |
| Glycerol | 3% |
| Demineralized water | up to 100% |

The cream obtained can be used in particular for the treatment of sensitive skin.

French priority document FR 96-03094 filed Mar. 12, 1996 is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A composition comprising a cosmetic active compound, a dermatological active compound, or a mixture thereof; at least one electrolyte; and an oily phase containing at least one polysaccharide alkyl ether gelling agent formed from a gum containing at least two different monosaccharide units, each unit containing at least one saturated alkyl ether group, wherein said gum is selected from the group consisting of guar gum, locust beam gum, karaya gum, gum tragacanth and mixtures thereof; wherein said oil phase comprises an oil selected from the group consisting of vegetable oil and fatty esters thereof, animal oil and fatty esters thereof, synthetic oil and fatty esters thereof, silicone oil, fluorinated oil, mineral oil, and mixtures thereof.

2. The composition of claim 1, in the form of an oily dispersion, a water-in-oil emulsion or an oil-in-water emulsion.

3. The composition of claim 1, wherein said saturated alkyl ether group contains 1 to 24 carbon atoms.

4. The composition of claim 1, wherein said saturated alkyl ether group contains 1 to 5 carbon atoms.

5. The composition of claim 1, wherein the alkyl of said saturated alkyl ether is selected from the group consisting of methyl, ethyl, n-propyl, isopropyl, n-butyl, isobutyl, tert-butyl chains and n-pentyl.

6. A process for treating skin and/or scalp and/or moisturizing the skin, comprising applying an effective amount of the composition of claim 1 to the skin or scalp.

7. The process of claim 6, wherein said skin or scalp is sensitive.

8. The composition of claim 1, wherein said polysaccharide alkyl ether has a weight average molecular weight greater than 200,000.

9. The composition of claim 1, wherein said polysaccharide alkyl ether is present in an amount ranging from 0.5 to 10 wt. % of the total weight of the composition.

10. The composition of claim 1, wherein said polysaccharide alkyl ether is present in an amount ranging from 2 to 8 wt. % of the total weight of the composition.

11. The composition of claim 1, wherein said electrolyte is present in a concentration ranging from 0.5 to 40 wt. % of the total weight of the composition.

12. The composition of claim 1, wherein said electrolyte is a salt of a mono-, di- or trivalent metal.

13. The composition of claim 12, wherein said salt is selected from the group consisting of barium, calcium, strontium, sodium, potassium, magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon and selenium salts, and mixtures thereof.

14. The composition of claim 13, wherein said electrolyte comprises an anion selected from the group consisting of chloride, borate, bicarbonate, carbonate, nitrate, hydroxide, sulfate, persulfate, glycerophosphate, acetate, anions of α-hydroxy acids, anions of fruit acids and anions of amino acids.

15. The composition of claim 1, wherein said electrolyte is selected from the group consisting of calcium, magnesium and strontium nitrate, calcium and magnesium borate, calcium, magnesium, sodium, strontium, neodymium and manganese chloride, magnesium and calcium sulfate, calcium and magnesium acetate, and mixtures thereof.

16. A process for the cosmetic or dermatological treatment of the skin, scalp, hair, nails or mucous membranes, comprising applying an effective amount of the composition of claim 1 to the skin, scalp, hair, nails or mucous membranes.

* * * * *